(12) United States Patent
Gocho (10) Patent No.: US 6,280,440 B1
(45) Date of Patent: Aug. 28, 2001

(54) CAUTERY APPARATUS

(75) Inventor: Masanori Gocho, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/307,436

(22) Filed: May 10, 1999

(30) Foreign Application Priority Data

May 13, 1998 (JP) ................................. 10-130490

(51) Int. Cl.[7] .................................................. A61B 18/18
(52) U.S. Cl. ............................... 606/41; 606/49; 604/151
(58) Field of Search ........................... 417/474, 477.2; 604/35, 30, 31, 131, 151, 152, 153; 606/27, 28, 31, 41, 46, 49

(56) References Cited

U.S. PATENT DOCUMENTS

| | | |
|---|---|---|
| 4,582,057 | 4/1986 | Auth et al. . |
| 4,691,703 | 9/1987 | Auth et al. . |
| 5,882,339 * | 3/1999 | Beiser et al. ......................... 604/153 |
| 6,027,502 * | 2/2000 | Desai ..................................... 606/41 |
| 6,077,246 * | 6/2000 | Kullas et al. ......................... 604/151 |

FOREIGN PATENT DOCUMENTS 6-18578    3/1994   (JP) .

* cited by examiner

Primary Examiner—Linda C. M. Dvorak
Assistant Examiner—David M. Ruddy
(74) Attorney, Agent, or Firm—Frishauf, Holtz, Goodman, Langer & Chick, P.C.

(57) ABSTRACT

The invention provides a cautery apparatus, which includes a cautery probe provided at the tip of a sheath that can be inserted into, for example, a treatment-tool channel of an endoscope, and also includes a liquid-supply pump to be connected to the sheath for supplying a liquid through nozzles formed in the cautery probe. The cautery apparatus comprises a pump driving motor provided in its main body, a pump unit containing the liquid-supply pump, an attaching device for detachably attaching the liquid-supply pump unit to the main body, and a coupling mechanism. The coupling mechanism couples the driving shaft of the liquid-supply pump to the driving shaft of the pump driving device to attach the liquid-supply pump unit to the main body, and separates the driving and driving shafts from each other to detach the liquid-supply pump unit from the main body.

16 Claims, 4 Drawing Sheets

CAUTERY APPARATUS

BACKGROUND OF THE INVENTION

This invention relates to a cautery apparatus having a main body equipped with a liquid-supply pump.

In general, endoscopes have a long, slim inserting section that is to be inserted into a body cavity without incising the body, in order to observe the interior of the cavity, or perform a diagnosis or various treatments therein. To this end, the inserting section of the endoscopes has a channel formed therein for inserting various treatment tools according to the conditions of a patient. While observing the interior of the body cavity, various treatments such as hemostasis of an ulcer are performed using the inserted treatment tools.

At present, multiple high-frequency current generators (hereinafter referred to as "cautery knives") are on the market. These generators are used to incise or coagulate tissue. In this technique, heat is generated by causing a high-frequency current to flow into body tissue. As a result, it is highly possible that the body tissue will be damaged to a certain degree, which is a limitation in the application of a treatment using a high-frequency current.

Tissue-coagulating apparatuses using a laser are also available at present. In this technique, however, it is difficult to accurately apply a laser beam to a target. Moreover, the laser apparatuses are expensive. In addition, handling the laser beam safely requires high-quality management and hence is troublesome.

Japanese Patent Application KOKOKU Publication No. 6-18578 discloses a cautery hemostatic probe using a Zener diode as a heat generator. This apparatus is easy to handle, which differs from the above-described apparatuses. Furthermore, the heat generator is not limited to the zener diode, but one that uses an electric resistor having a temperature coefficient is also proposed.

The above-described cautery apparatuses employ a liquid supply function as well. This function is used to wash away bled blood to clarify the position of the bleeding. To effect the function, a liquid-supply pump is contained in the cautery apparatuses.

In the cautery hemostatic apparatuses which use the liquid supply function effected by the liquid-supply pump, it is desirable that the interior of the pump and the liquid supply pipes should be disinfected and sterilized.

However, the apparatus disclosed in Japanese Patent Application KOKOKU Publication No. 6-18578 has a structure in which a piston pump is fixed in the apparatus body, which limits the methods of disinfecting and sterilizing the pump, and also requires a lot of time and effort to execute the disinfection or sterilization.

BRIEF SUMMARY OF THE INVENTION

It is the object of the invention to provide a cautery apparatus provided with a liquid-supply pump unit that can be detached from the main body of the apparatus and can be disinfected and sterilized easily.

To attain the aim, the invention provides a cautery apparatus including a liquid-supply pump to be connected to a sheath for supplying a liquid into a probe that is to be inserted into a body cavity of a patient for cauterizing tissue therein, comprising:

a main body;

a pump driving device provided in the main body;

a liquid-supply pump unit containing the liquid-supply pump therein and having a casing;

an attaching device for detachably attaching the liquid-supply pump unit to the main body; and a coupling mechanism for coupling a driving shaft of the liquid-supply pump to a driving shaft of the pump driving device to attach the liquid-supply pump unit to the main body, and separating the driving and driving shafts from each other to detach the liquid-supply pump unit from the main body.

In the invention constructed as above, the liquid-supply pump unit can be detached from the main body of the apparatus, whereby the liquid-supply pump can be easily disinfected and sterilized. In other words, disinfection or sterilization of the liquid-supply pump is not limited to a particular method and does not require a lot of time and effort.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION (First Embodiment)

Figure 1:
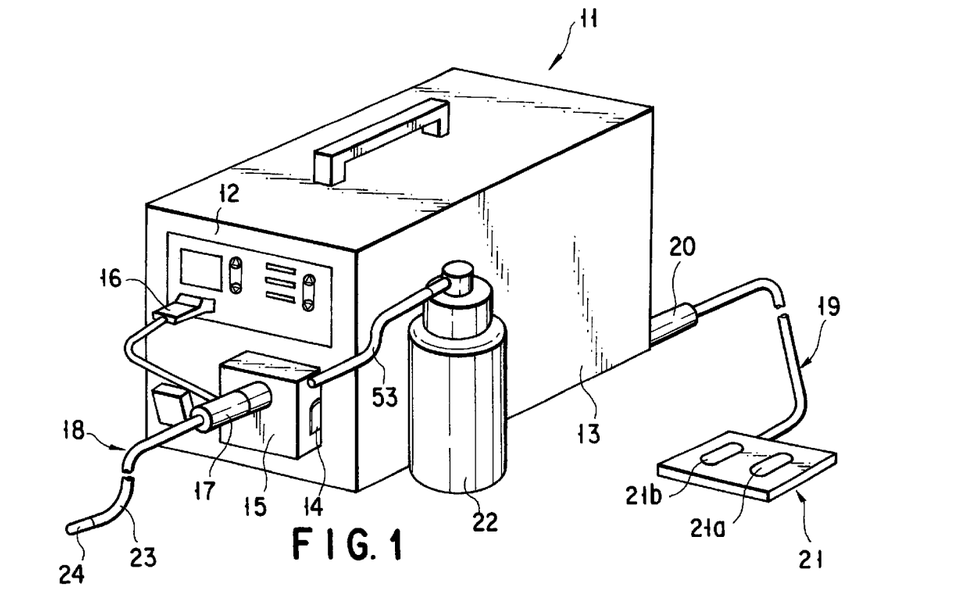
FIG. 1 is a view showing an outward appearance of a cautery hemostatic apparatus according to a first embodiment of the invention.

Referring first to FIGS. 1, 3, 4A, 4B, 5–11, 12A and 12B, a cautery hemostatic apparatus 11 according to a first embodiment of the invention will be described. As is shown in FIG. 1, the cautery hemostatic apparatus 11 has a main body 13 in the form of a box, and an operation panel 12 provided on the front wall of the main body 13.

A liquid-supply pump 15 is detachably attached to the front wall of the main body 13. Specifically, the liquid-supply pump 15 is attached to the main body 13 by means of claws 14 as attaching means, which will be described later. Further, a cautery hemostatic probe 18 is detachably attached to the main body 13. The cautery hemostatic probe 18 has an electric connector 16 and a liquid-supply connector 17. The liquid-supply pump unit 15 is disconnectably connected to a connecting section of the main body 13 via the electric connector 16. The liquid-supply connector 17 is connectable to the liquid-supply pump unit 15, and communicates with a liquid-supply pump, described later, when it is connected.

A foot switch 21 is disconnectably connected to the main body 13. The switch 21 has a cable 19, and is connected to a rear portion of the main body 13 by means of a connector 20 provided on the cable 19. The switch 21 also has a switch 21a for liquid supply and a switch 21b for heating.

A rinse tank 22 is detachably attached to an outer wall of the main body 13.

The cautery hemostatic probe 18 comprises a slim, flexible sheath 23, a cautery probe 24 connected to the front end of the sheath 23, and the electric connector 16 and the liquid-supply connector 17 provided at the proximal end of the sheath 23. The sheath 23 and the cautery probe 24 are to be inserted into treatment-tool inserting channels formed in an endoscope (not shown), so that the probe 24 will be introduced into a cavity of a patient's body.

Figure 2:
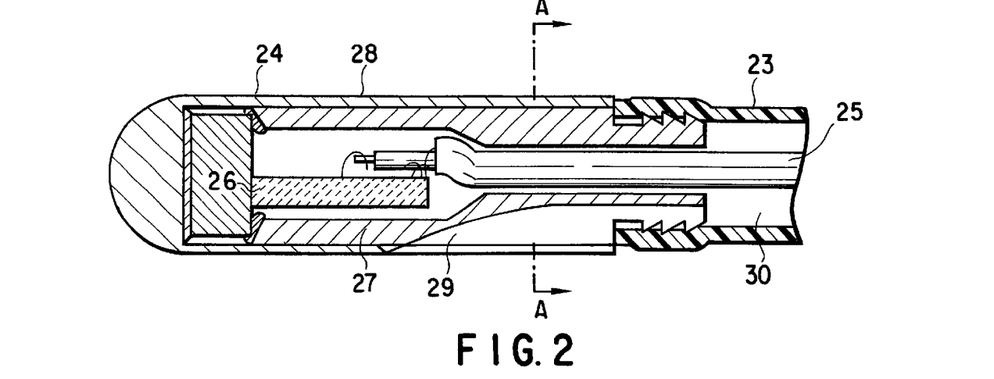
FIG. 2 is a sectional view illustrating a heat probe incorporated in the apparatus of FIG. 1.

As is shown in FIG. 2, a cable 25 coaxial with the sheath 23 is inserted therein. A resistor 26 as the heat generator in the cautery probe 24 is supplied with a current via the coaxial cable 25.

Figure 3:
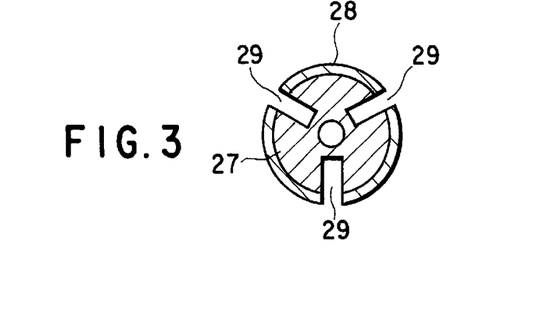
FIG. 3 is a sectional view taken along lines A—A of FIG. 2 and showing part of the heat probe.

As is shown in FIGS. 2 and 3, a plurality of long nozzles 29 in the form of grooves extend axially and radially in a main body member 27 and a cover member 28 incorporated in the probe 24, and also in the sheath 23. A passage defined in the sheath 23 communicates with the nozzles 29 and forms a liquid-supply passage 30 for pressure-supplying a rinse. The rinse supplied through the liquid-supply passage 30 is discharged as a jet through the nozzles 29.

Figure 4A:
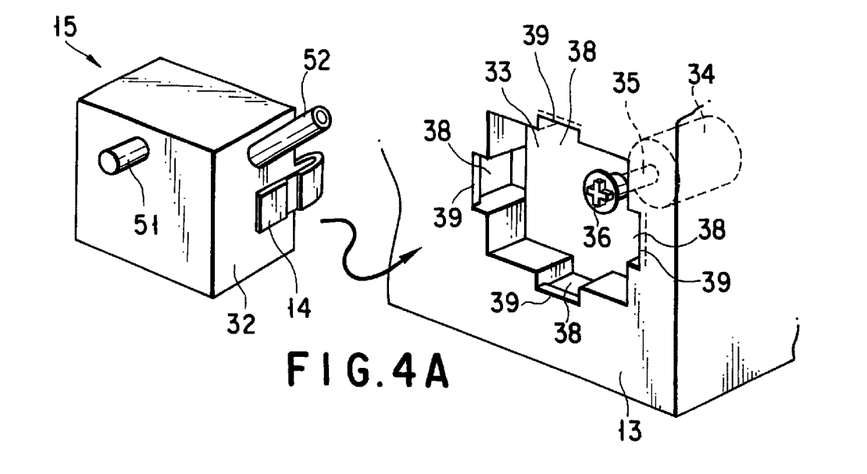
FIG. 4A is a view useful in explaining how a liquid-supply pump unit is attached to a main body of the apparatus of the first embodiment.
Figure 4B:
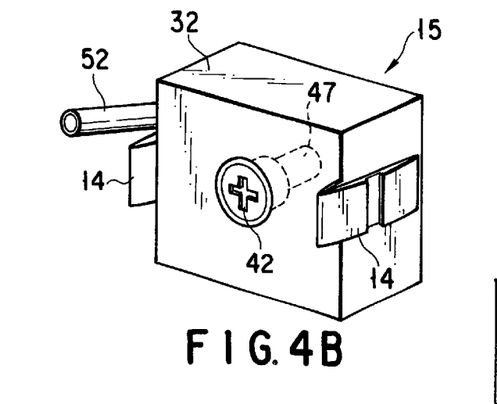
FIG. 4B is a view showing an outward appearance of the liquid pump unit.

The structure of a medical liquid-supply unit incorporated in the cautery hemostatic apparatus 11 of the first embodiment will be described in detail. FIG. 4A and FIG. 4B show the structure of an attaching device for detachably attaching the liquid-supply pump unit 15 to the main body 13.

The casing 32 of the liquid-supply pump unit 15 is in the form of a rectangular box that has square front and rear surfaces. The casing 32 can be fitted into a pump-unit fitting recess 33 formed in the front wall of the main body 13. Since the front and rear surfaces of the casing 32 are square, it can be fitted with the angle of position changed by 90° or 180°.

Usually, the liquid-supply pump unit 15 is fitted in the main body 13 with the claws 14 situated on the right-hand and left-hand as shown in FIG. 4A and FIG. 4B. If the casing 32 has rectangular front and rear surfaces, it is fitted in the aforementioned position. The engagement claws 14 are formed by bending a spring plate. The claws 14 are attached to respective side surfaces of the casing 32 of the liquid-supply pump unit 15.

As is shown in FIG. 4A, a pump driving motor 34 as pump driving means is located in the main body 13. The front end of the driving shaft 35 of the motor 34 extends through the front wall of the main body 13 and protrudes in the recess 33. A spline shaft 36 is formed at the front end of the driving shaft 35 which protrudes in the recess 33. The driving shaft 35 exposes only the spline shaft 36 in the recess 33.

Grooves 38 for receiving the claws 14 of the liquid-supply pump unit 15 are formed in respective four walls which define the recess 33. Four grooves 38 are provided so that the claws 14 can be fitted therein even when the angle of position of the liquid-supply pump unit 15 is changed by 90° or 180°.

A holding member 39 to be engaged with the claws 14 of the liquid-supply pump unit 15 projects from the front edge of each groove 38. When the casing 32 of the pump unit 15 is fitted in the recess 33 of the main body 13, the claws 14 are engaged with corresponding ones of the holding members 39, thereby holding the pump unit 15. Thus, the liquid-supply pump unit 15 is detachably attached to the main body 13.

Figure 5:
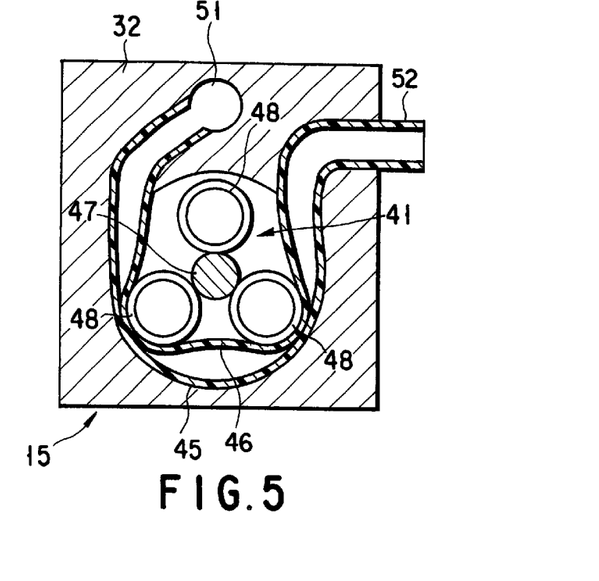
FIG. 5 is a sectional view illustrating a liquid-supply pump unit which contains a roller pump.

A liquid-supply pump 41 is provided in the casing 32 of the liquid-supply pump unit 15 as shown in FIG. 5. The casing 32 protects the liquid-supply pump 41 from external factors. The rear surface of the casing 32 has a spline shaft receiving recess 42 exposed therein as shown in FIG. 4B. The spline shaft receiving recess 42 is formed in an end of the driving shaft 47 of the pump 41 for receiving the spline shaft 36.

It is preferable to use, as the liquid-supply pump 41 of the pump unit 15, for example, a roller pump as shown in FIG. 5, which can be disinfected or sterilized in various manners, and can perform automatic priming.

In a roller pump shown in FIG. 5, a circumferential groove 45 is formed in the casing 32, and an intermediate portion of an elastic tube 46 is fitted in the groove 45. At a central portion around which the circumferential groove 45 extends, the driving shaft 47 coupled to the spline shaft 36 is passed. Three rollers 48 are provided around the driving shaft 47. In accordance with the rotation of the driving shaft 47, the three rollers 48 revolve around the driving shaft 47 while rotating, thereby sequentially squashing the intermediate portion of the tube 46 located in the circumferential groove 45. As a result, a liquid in the tube is forwarded.

A first port 51 that communicates with one end of the tube 46 of the roller pump is formed in the front wall of the casing 32. The liquid-supply connector 17 of the cautery hemostatic probe 18 is disconnectably connected to the first port 51. A second port 52 that communicates with the other end of the tube 46 of the roller pump is formed in a side wall of the casing 32. A liquid-supply tube 53 (see FIG. 1) that communicates with the rinse tank 22 is connected to the second port 52.

When the liquid-supply pump unit 15 has been fitted into the recess 33 of the main body 13, the spline shaft receiving recess 42 in the pump unit 15 is engaged with the spline shaft 36 of the main body 13, thereby coupling, the shaft of the liquid-supply pump 41 to the shaft of the pump driving means. On the other hand, when the liquid-supply pump unit 15 is removed from the main body 13, the shafts of the pump 41 and the pump driving means are separated from each other. The spline shaft 36, the spline shaft receiving recess 42 and the shafts of the pump 41 and the pump driving means constitute a coupling mechanism.

When the pump driving motor 34 has operated, its rotation is transmitted to the driving shaft 47 of the liquid-supply pump unit 15 via the driving shaft 35, thereby operating the liquid-supply pump 41.

Although both the spline shaft 36 and the spline shaft receiving recess 42 for receiving the shaft 36 are cross-shaped as shown in FIG. 4A and FIG. 4B, their shape is not limited to it. It suffices if they are attachable to each other and detachable from each other.

As described above, the use of the spline shaft 36 and the shaft receiving recess 42 enables separation of the driving shaft 35 of the pump driving motor 34 from the driving shaft 47 of the liquid-supply pump 41. Further, claws 14 of the same shape as attachment/detachment means are provided on various types of liquid-supply pump units 15 containing different types of liquid-supply pumps that can be disinfected and sterilized in various manners and can perform automatic priming. This enables attachment, to the main body 13 of the cautery hemostatic apparatus, of one of the liquid-supply pump units 15 which is suitable for the conditions of a patient.

Moreover, a piston pump, a geared pump, etc. can be used as the liquid-supply pump that can be disinfected and sterilized and can perform automatic priming, as well as the roller pump. If the same attaching device and coupling device are commonly employed, the casings 32 of liquid-supply pump units 15 may have different shapes between different types.

Figure 6:
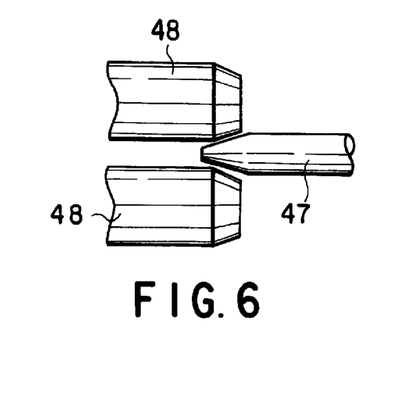
FIG. 6 is a view useful in explaining a roller and a driving shaft that is disposed to be attachable to and detachable from the liquid-supply pump of the pump unit.

In the liquid-supply pump unit 15 constructed as above, in order to disinfect or sterilize the liquid-supply pump 41 in a reliable manner, the driving shaft 47 of the liquid-supply pump 41 may be pulled out of the liquid-supply pump unit 15, or may be displaced axial or parallel to the axis to release the tube 46 from its closed state, using its elasticity. In this case, to facilitate the re-insertion of the driving shaft 47 of the liquid-supply pump 41, a peripheral portion of each roller 48 and an insertion-side end portion of the driving shaft 47 may be tapered as shown in FIG. 6.

Figures 7, 8:
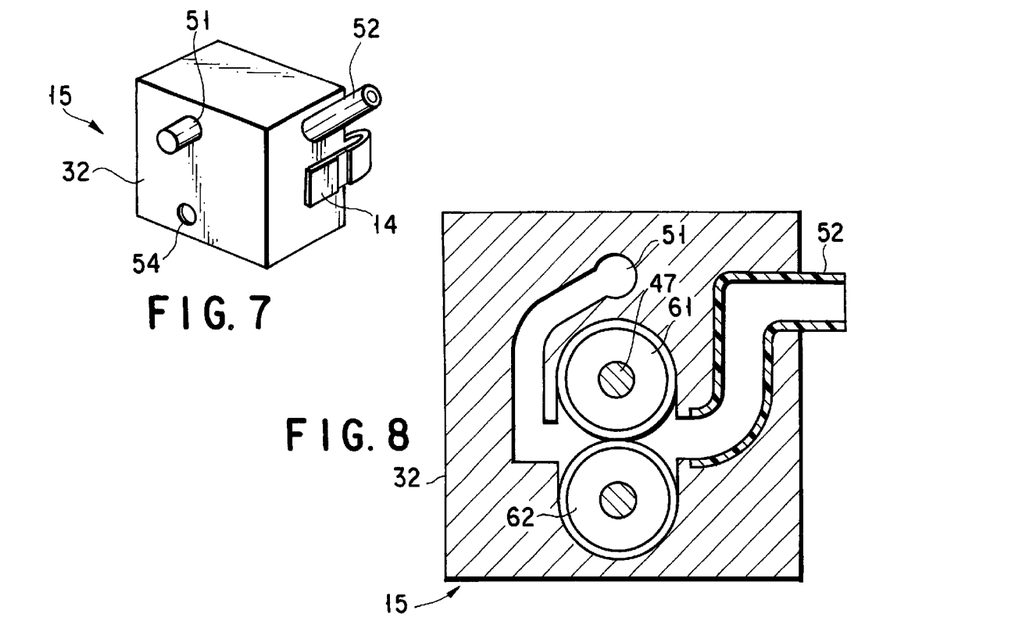
FIG. 7 is a view showing an outward appearance of a liquid-supply pump unit that has a drain port.
FIG. 8 is a sectional view illustrating a liquid-supply pump unit that contains a geared pump.

In addition, it is possible in the roller pump that the peripheral wall of the tube 46 will crack as a result of repetition of squashing, and a liquid will leak to the casing 32 through the crack. To avoid this, the pump unit 15 may be modified such that a drain port 54 is formed in the casing 32 below the driving shaft 47 of the liquid-supply pump 41, as is shown in FIG. 7. The drain port 54 may be connected to a tube (not shown) through which a leaked liquid will return into the rinse tank 22.

Referring then to FIG. 8, a liquid-supply pump unit 15 using a geared pump as the liquid-supply pump 41 will be described. The casing 32 of the liquid-supply pump unit 15 contains a first gear 61 coupled to the liquid-supply pump driving shaft 47, and a second gear 62 which moves in synchronism with the first gear 61. While the driving shaft 47 rotates, the first and second gears 61 and 62 which are engaged with each other rotate, thereby forwarding a liquid.

The liquid-supply pump 41 of the liquid-supply pump unit 15 may be formed of a piston pump (not shown), which can be also simply arranged in the unit.

Thus-protecting the liquid-supply pump of the liquid-supply pump unit 15 with the casing 32 using the spline shaft 36 and the spline shaft receiving recess 42 enables realization of a liquid-supply pump unit containing a detachable liquid-supply pump that can be disinfected and sterilized and can perform automatic priming. Accordingly, an appropriate one of two or more types of liquid-supply pump units 15 that contain liquid-supply pumps of different types or capacities can be connected for use to the cautery hemostatic apparatus 11.

A control system for driving the aforementioned two or more liquid-supply pump units 15 will now be described.

Figure 9:
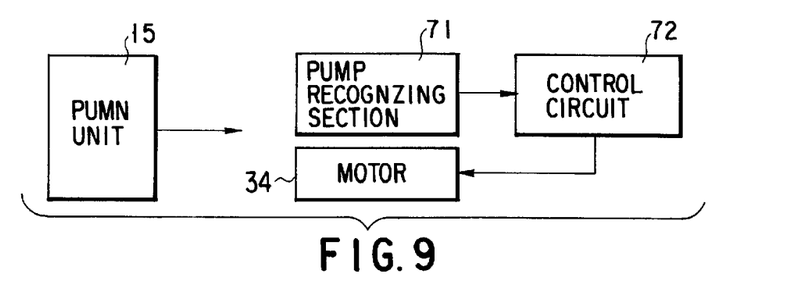
FIG. 9 is a schematic diagram illustrating a pump control method.

To drive the liquid-supply pump of various types of liquid-supply pump units 15 using the pump driving motor 34 incorporated in the main body 13, the motor 34 must have different rotational-speed/torque characteristics. To this end, it is necessary to recognize, using a pump recognizing section 71, one of the liquid-supply pump units 15 which is connected to the main body 13 to thereby determine the type of the connected liquid-supply pump, and then to control, using a control circuit 72, the pump driving motor 34 in accordance with the determined pump type. As a result, the motor 34 can perform an appropriate driving operation for the determined pump type.

Figure 10:
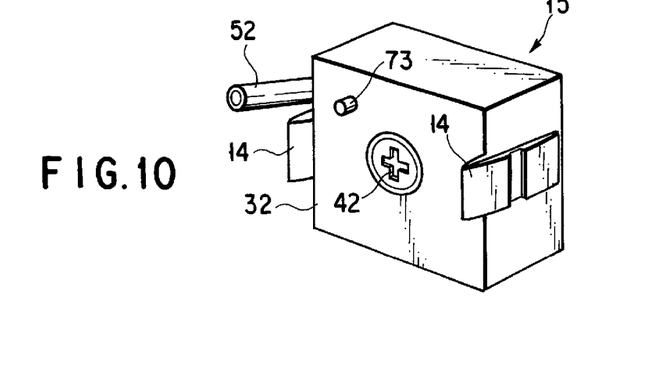
FIG. 10 is a perspective view illustrating a modification of the casing of the liquid-supply pump unit.

The pump recognizing section 71 for recognizing the type of the connected liquid-supply pump unit 15 will be described. As is shown in FIG. 10, a projection 73 to be inserted into the liquid-supply pump unit mounting recess 33 of the main body 13 of the cautery hemostatic apparatus 11 is provided on the reverse surface of the casing 32 of the liquid-supply pump unit 15. The location of the projection 73 is predetermined on the basis of the type or the capacity of the liquid-supply pump of the pump unit 15.

Figure 11:
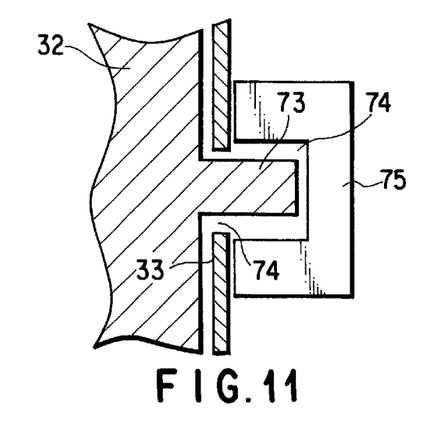
FIG. 11 is a view showing the structure of a pump recognizing section.

Further, as is shown in FIG. 11, a plurality of holes 74 are formed in the bottom of the liquid-supply pump unit mounting recess 33 of the main body 13 at locations corresponding to the projections 73 of the various types of liquid-supply pump units 15. When one of the liquid-supply pump units 15 has been fitted in the recess 33, the projection 73 of the unit 15 is inserted in a corresponding one of the holes 74. A photo coupler 75 is provided inside the each hole 74 such that it surrounds the axis of the hole.

Where one of the liquid-supply pump units 15 is fitted in the recess 33, its projection 73 is inserted into a corresponding one of the holes 74, thereby shifting the photo coupler 75 to its turn-off state. As a result, the type of the pump provided in the liquid-supply pump unit 15 is recognized.

As described above, the apparatus of the invention is compatible with two or more different types of liquid-supply pump units 15, and can perform an appropriate operation in accordance with the type of a pump contained in each liquid-supply pump unit 15. The apparatus of the invention can perform an appropriate treatment by attaching, to the main body 13, a liquid-supply pump unit 15 that contains a pump suitable for the conditions of a patient. Furthermore, even while one of the pumps is disinfected or sterilized, the apparatus of the invention can be operated using another pump, which differs from the conventional cautery apparatuses with a built-in pump. In other words, the apparatus of the invention can be used any time.

The means for recognizing the type of a liquid-supply pump contained in a liquid-supply pump unit 15 connected to the main body 13 is not limited to the photo coupler, but may be a switch (not shown) for detecting the projection 73. In addition, the structure of the apparatus may be modified such that a projection similar to the projection 73 is provided on a switch section that is arranged on the main body side, while a recess to be engaged with the projection is formed in each liquid-supply pump unit 15. This structure also can recognize the type of a pump contained in a connected one of the liquid-supply pump units 15. Instead of the combination of the projection and the recess, a sensor such as an infrared sensor or a magnetic sensor may be provided on the main body side, and an object to be sensed by it be provided on the pump unit side.

In the case of, for example, a roller pump as shown in FIG. 5, its rotational speed must be set at a high value although its torque may be set at a low value. On the other hand, in the case of a piston pump not shown, its torque must be set at a high value although its rotational speed may be set at a low value. Thus, the rotational-speed/torque control circuit is constructed to drive the motor 34 on the basis of the known characteristics of the pumps, so that one of the pumps which is connected to the main body 13 can have an appropriate rotational speed and torque. As a result, each pump can be controlled in an optimal manner.

Figure 12A:
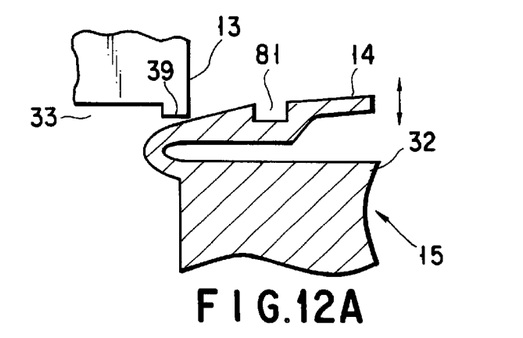
FIG. 12A and FIG. 12B are views useful in explaining the attachment of fixing means to the main body of the liquid-supply pump unit.

Various methods can be considered for fixing the liquid-supply pump unit 15 to the recess 33 of the main body 13. For example, as is shown in FIG. 12A, each engagement claw 14 may be formed of an elastic member, and have a groove 81 for receiving the holding member 39 when a front portion of the claw 14 is elastically fitted into the recess 33. When the claw 14 has been pushed against its elastic force, the holding member 39 and the groove 81 are disengaged from each other, thereby permitting the liquid-supply pump unit 15 to be removed from the recess 33 of the main body 13.

Figure 12B:
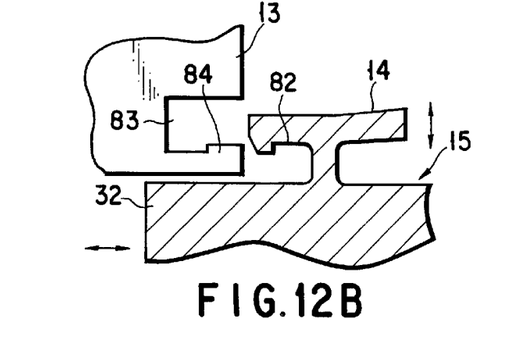

Further, as is shown in FIG. 12B, each engagement claw 14 may have a seesaw structure with a claw 82 at one end. When the claw 82 has been fitted into an engagement recess 83 formed in the wall of the main body 13, it is automatically engaged with a holding portion 84 due to its own elastic force. When, on the other hand, the other end of the claw 14 has been pushed, the claw 82 is swung like a seesaw and disengaged from the holding portion 84 of the engagement recess 83. As a result, the liquid-supply pump unit 15 is removed from the recess 33 of the main body 13. Thus, various types of attaching means can be employed.

Furthermore, if the liquid-supply pump unit 15 is constructed such that the casing 32 can be fitted into the recess 33 with the angle of position changed by 90° or 180°, the direction of the casing 32 can be recognized using the same structure as the pump recognizing section 71. When the liquid-supply pump unit 15 is fitted into the recess 33 with the angle of position changed, the positions of the suction port and the discharge port of the pump unit 15 will change. In the cases of the roller pump of FIG. 5 and the geared pump of FIG. 8, the suction port can be used as the discharge port and vice versa by constructing the control section so as to change the direction of rotation of the motor in accordance with the direction of flow in the liquid-supply pump of the pump unit 15. This structure increases the degree of freedom in direction in which the liquid-supply pump is arranged in accordance with a treatment tool, thereby facilitating the operation of the cautery apparatus.

In the first embodiment, the spline shaft receiving recess 42 is provided in the driving shaft 47 of the pump 41 of the liquid-supply pump unit 15, while the spline shaft 36 to be engaged with the spline shaft receiving recess 42 is provided on the driving shaft 35 of the driving means on the main body 13 side. This structure enables simple and easy attachment and detachment of the liquid-supply pump unit 15 to and from the main body 13, and also enables simple and easy exchange of one unit with another. Accordingly, any one of liquid-supply pump units 15 that contain different types of liquid-supply pumps can be optionally used. Selection of a liquid-supply pump unit 15 which contains a pump suitable for a treatment enables more reliable and effective execution of the treatment. Also, control means for driving the driving means in accordance with the type of a liquid-supply pump recognized by the pump recognizing means (which is disposed to recognize the type of a liquid-supply pump unit based on the type of a pump contained therein) permits the liquid-supply pump to be disinfected and sterilized easily, as compared with an apparatus in which the liquid-supply pump is incorporated in the main body 13.

(Second Embodiment)

Figure 13:
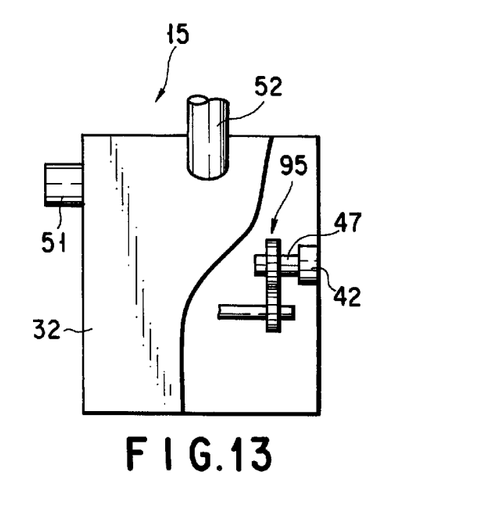
FIG. 13 is a view useful in explaining a liquid-supply pump unit according to a second embodiment.

Referring now to FIG. 13, a second embodiment of the invention will be described. The second embodiment employs, in place of the pump recognizing means in the first embodiment, acceleration/deceleration means 95 which is formed of, for example, a gear mechanism and adapted for the characteristics of a liquid-supply pump contained in the liquid-supply pump unit 15. The driving force transmitted from the spline shaft receiving recess 42 is sent to the liquid-supply pump via the driving shaft 47 and the acceleration/deceleration means 95, thereby driving the pump. Setting of the acceleration/deceleration means 95 is performed in accordance with the characteristics of the liquid-supply pump.

In the second embodiment, the gear ratio of the acceleration/deceleration means 95 is set so that the liquid-supply pump contained in the pump unit 15 can have an appropriate rotational speed. Accordingly, it is not necessary to employ pump recognizing means as used in the first embodiment. In other words, the pump driving means can drive the pump so as to operate at a predetermined rotational speed, without the pump recognizing means.

Since the second embodiment does not require the pump recognizing means, the entire structure of the apparatus can be simplified. As a result, a larger number of types of pump units than in the first embodiment can be attached to the main body of the apparatus.

(Third Embodiment)

In the first embodiment, a resistor is used as a heat generator in the cautery probe 24 of the cautery hemostatic apparatus 11. In this case, constant temperature control in which heat generation is carried out at a constant temperature is employed, and the temperature for heat generation is detected by feeding back a change in impedance of the resistor 26 as the heat generator contained in the cautery probe 24. Although in this method, the heat generator is subjected to constant-temperature control, the actual surface temperature of the cautery probe 24 to be brought into contact with living tissue varies between portions thereof due to variations in heat radiation.

Figure 14A:
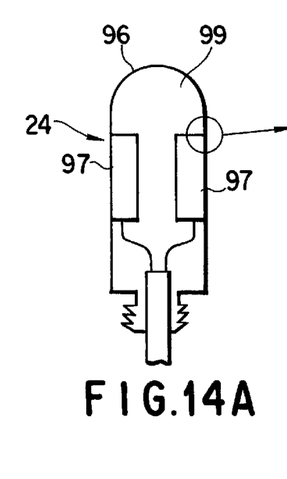
FIG. 14A and FIG. 14B are views useful in explaining a structure in which a probe heat generator is formed in a lower layer of attachment preventing coating provided on the surface of a probe.
Figure 14B:
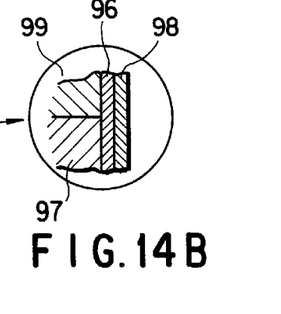

To improve it, the third embodiment employs a resistance thin film 96 with a temperature coefficient formed on the surface of the probe, and electrodes 97 provided on opposite sides of the film 96, as is shown in FIG. 14A and FIG. 14B. Adhesion preventing coating 98 may be formed on the thin film 96. The probe main body 99 of the probe 24, which is provided between the electrodes 97 and in contact with the resistance thin film 96, is formed of an electrical insulator, and the adhesion preventing coating 98 also serves as an electrical insulator. To increase the mechanical strength, the adhesion preventing coating 98 may be covered with another insulator or a metal member.

When in this case, a power has been supplied from the main body 13 to the electrodes 97, a current flows through the resistance thin film 96 interposed as a heat generator between the electrodes 97. If the adhesion preventing coating 98 does not serve as an electrical insulator, an insulating film is formed between the resistance thin film 96 and the adhesion preventing coating 98 (this structure is not shown).

Since in the third embodiment, the resistance thin film 96 is uniformly provided on the lower surface of the adhesion preventing coating 98, the surface temperature of the probe can be set at substantially the same value as the temperature of the heat generator. Also, it is not necessary to make a current flow into living tissue. Accordingly, the application range of this apparatus can be increased. Furthermore, the degree of freedom in the shape of the probe is higher than the conventional apparatus in which the heat generator is located within the probe.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cautery apparatus including a liquid-supply pump connected to a sheath for supplying a liquid into a probe that is inserted into a body cavity of a patient for cauterizing tissue therein, comprising:

a main body;

a pump driving device provided in the main body;

a liquid-supply pump unit detachedly provided in the main body, the liquid-supply pump unit containing the liquid-supply pump therein and having a casing;

a cautery probe connected to the liquid-supply pump unit, and having a passage connected to a passage provided in the liquid-supply pump unit;

an attaching device for detachably attaching the liquid-supply pump unit to the main body; and a coupling mechanism for coupling a driving shaft of the liquid-supply pump to a driving shaft of the pump driving device when the liquid-supply pump unit is attached to the main body, and separating the driving shafts of the liquid supply pump and the pump driving device from each other when the liquid-supply pump unit and the main body are detached from each other.

2. A cautery apparatus according to claim 1, wherein the liquid-supply pump unit is attached to the exterior of the main body.

3. A cautery apparatus according to claim 1, further comprising a liquid-supply tank provided outside the main body and connected to the liquid-supply pump of the liquid-supply pump unit.

4. A cautery apparatus according to claim 1, wherein the attaching device includes:

a fitting recess formed in the main body for fitting therein at least part of the casing of the liquid-supply pump unit; and a detachable holding member for holding the casing in a position in which the at least part of the casing of the liquid-supply pump unit is fitted in the fitting recess.

5. A cautery apparatus according to claim 1, wherein
    the attaching device includes an elastic claw provided on the main body side, and a holding portion provided on the liquid-supply pump unit side and engaged with the elastic claw, and
    the elastic claw is automatically engaged with the holding portion when the liquid-supply pump unit is situated in an attachment position in the main body, and is deformed and released from the holding portion when an external force has been applied thereto.

6. A cautery apparatus according to claim 1, wherein the coupling mechanism employs a spline-shaft structure.

7. A cautery apparatus according to claim 1, wherein the liquid-supply pump unit has a speed-change device for changing a rotational speed to be transmitted from the driving shaft of the pump driving device to the driving shaft of the liquid-supply pump, and transmitting the changed rotational speed to the liquid-supply pump.

8. A cautery apparatus according to claim 1, wherein the liquid-supply pump of the liquid-supply pump unit is a roller pump, and has a drain port as an exhaust.

9. A cautery apparatus according to claim 1, wherein the pump driving device drives a flow in the liquid-supply pump in opposite directions of rotation.

10. A cautery apparatus according to claim 1, wherein the cauterizing probe is coated with a coating for preventing adhesion of living tissue to the probe, and has a thin film resistor as a heat generator uniformly formed under the coating, and electrodes for supplying a power to the thin film resistor.

11. A cautery apparatus including a liquid-supply pump connected to a sheath for supplying a liquid into a probe that is to be introduced into a body cavity of a patient for cauterizing tissue therein, comprising:

a main body;

a pump driving device provided in the main body;

plural types of liquid-supply pump units being detachably provided in the main body, each containing a liquid-supply pump therein and having a casing;

a cautery probe connected to each liquid-supply pump unit, and having a passage connected to a passage provided in each liquid-supply pump unit;

an attaching device for detachably attaching one of the liquid-supply pump units to the main body; and a coupling mechanism for coupling a driving shaft of the liquid-supply pump of the one of the liquid-supply pump units to a driving shaft of the pump driving device when the liquid supply pump unit is attached to the main body, and separating the driving shafts of the liquid-supply pump and the pump driving device from each other when the liquid-supply pump unit and the main body are detached from each other.

12. A cautery apparatus according to claim 11, wherein the coupling mechanism employs a spline-shaft structure.

13. A cautery apparatus according to claim 11, wherein the plural types of liquid-supply pump units contain liquid-supply pumps of different liquid supply-capacities.

14. A cautery apparatus according to claim 11, wherein the casings of the plural types of liquid-supply pump units have different shapes.

15. A cautery apparatus according to claim 11, further comprising:

a pump recognizing device for detecting a difference in shape between the casings of the liquid-supply pump units, thereby recognizing the type of a liquid-supply pump contained in one of the liquid-supply pump units which is attached to the main body, the difference in shape between the casings corresponding to a difference in type between the liquid-supply pumps; and a control device for controlling one of the liquid-supply pumps which is recognized by the pump recognizing device, in accordance with liquid supply characteristics of the one of the liquid-supply pumps.

16. A cautery apparatus according to claim 11, further comprising:

a pump recognizing device for detecting a difference in shape between the casings of the liquid-supply pump units, thereby recognizing the type of a liquid-supply pump contained in one of the liquid-supply pump units which is attached to the main body, the difference in shape between the casings corresponding to a difference in type between the liquid-supply pumps, and the liquid-supply pump units being attached to the main body with their angular positions changed in accordance with the types of the liquid-supply pumps contained therein; and a control device for controlling one of the liquid-supply pumps which is recognized by the pump recognizing device, in accordance with liquid supply characteristics of the one of the liquid-supply pumps, the control device controlling driving conditions including rotational speed, torque, driving direction, of the one of the liquid-supply pumps in accordance with a direction of the liquid-supply pump unit recognized by the pump recognizing device.

* * * * *